United States Patent [19]

Johnson et al.

[11] 4,274,414
[45] Jun. 23, 1981

[54] SURGICAL INSTRUMENT

[75] Inventors: Lanny L. Johnson, Okemos, Mich.; Leonard J. Bonnell, Medford, Mass.

[73] Assignee: Dyonics, Inc., Woburn, Mass.

[21] Appl. No.: 13,407

[22] Filed: Feb. 21, 1979

[51] Int. Cl.³ ............................................. A61B 17/32
[52] U.S. Cl. ................................................... 128/305
[58] Field of Search ..................... 128/305, 751–755, 128/304, 276, 307, 309, 312, 757–758; 30/240

[56] References Cited

U.S. PATENT DOCUMENTS

| | | | |
|---|---|---|---|
| 1,262,536 | 4/1918 | Martin | 30/240 |
| 1,493,240 | 5/1924 | Bohn | 128/305 |
| 1,663,761 | 3/1928 | Johnson | 128/305 |
| 2,369,925 | 2/1945 | Smith | 128/317 |
| 3,618,611 | 11/1971 | Urban | 128/305 |
| 3,732,858 | 5/1973 | Banko | 128/305 X |
| 3,734,099 | 5/1973 | Bender et al. | 128/305 |
| 3,844,272 | 10/1974 | Banko | 128/305 X |
| 3,937,222 | 2/1976 | Banko | 128/305 |
| 3,945,375 | 3/1976 | Banko | 128/6 |
| 3,976,077 | 8/1976 | Kerfoot | 128/305 |
| 3,996,935 | 12/1976 | Banko | 128/276 |

Primary Examiner—Robert W. Michell
Assistant Examiner—Michael H. Thaler
Attorney, Agent, or Firm—John N. Williams

[57] ABSTRACT

Remote-cutting instrument formed by an inner tube rotating within an outer tube, in which an initial cutting point where portions of the tubes first come together during a cutting cycle is defined at the distal extremity of the sides of the tubes and cutting edges extend from this initial point longitudinally along the sides of the tubes. The coacting side edges of the tubes diverge in the proximal direction. There are end cutting edges of circular form, defining cusp-shaped points.

12 Claims, 13 Drawing Figures

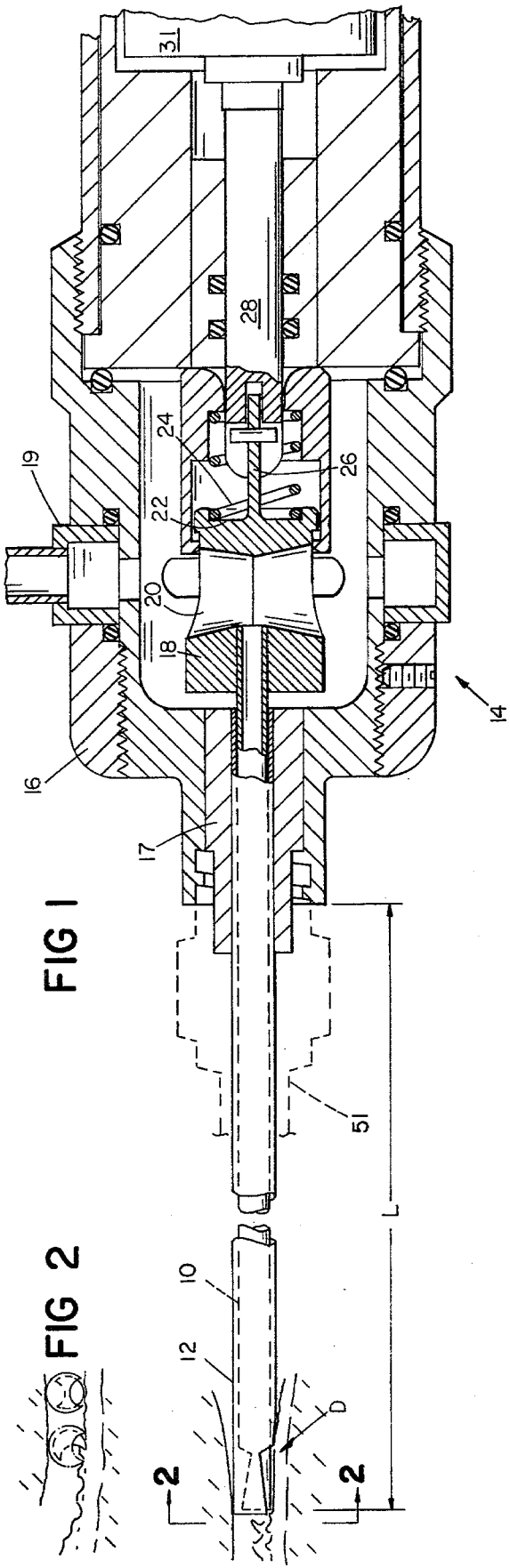
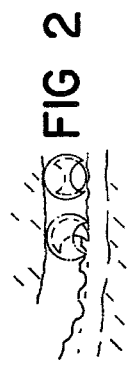
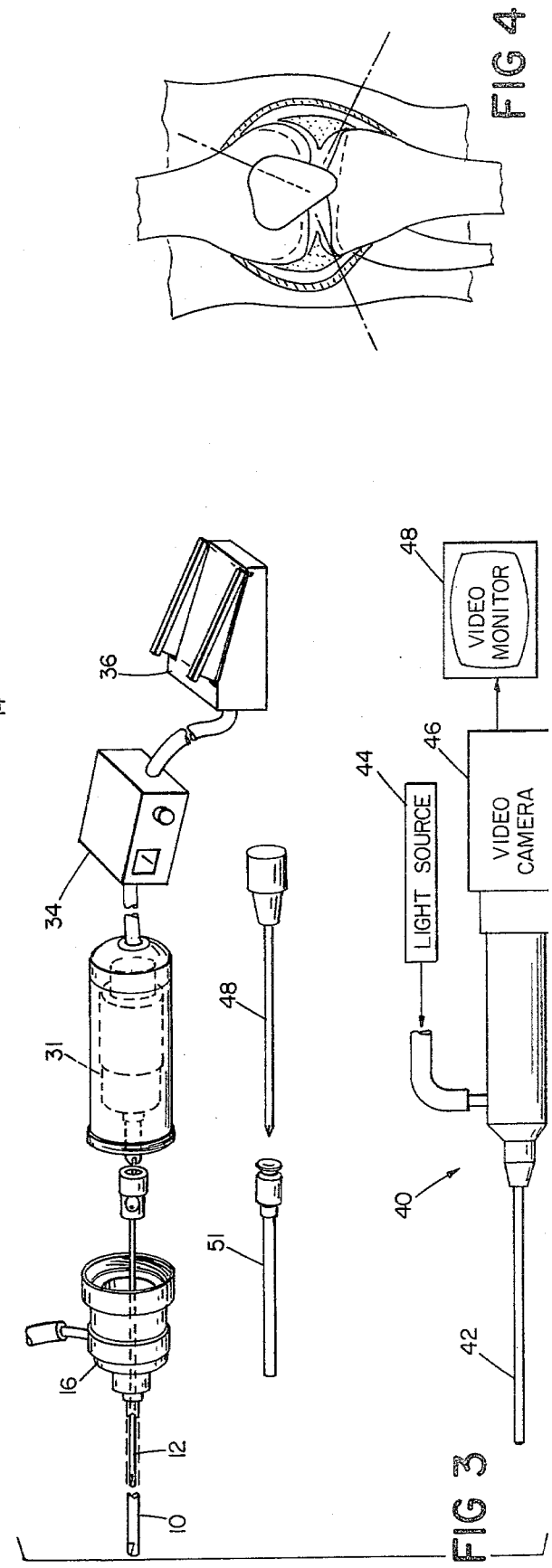
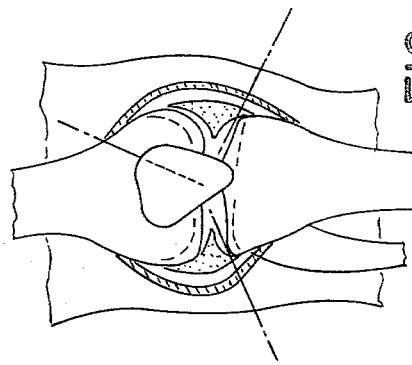

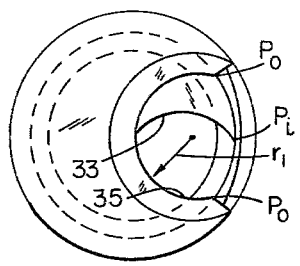
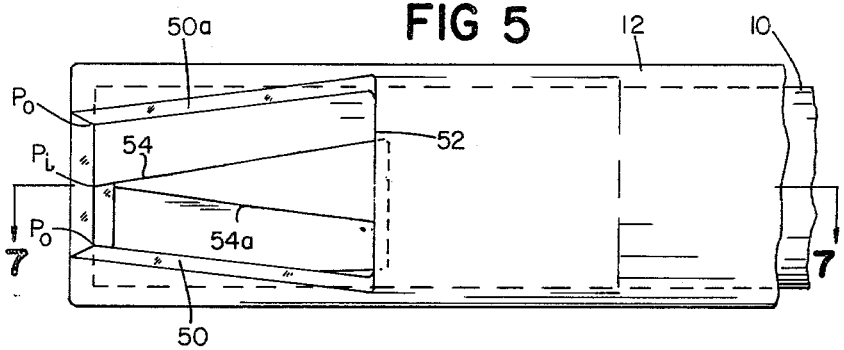
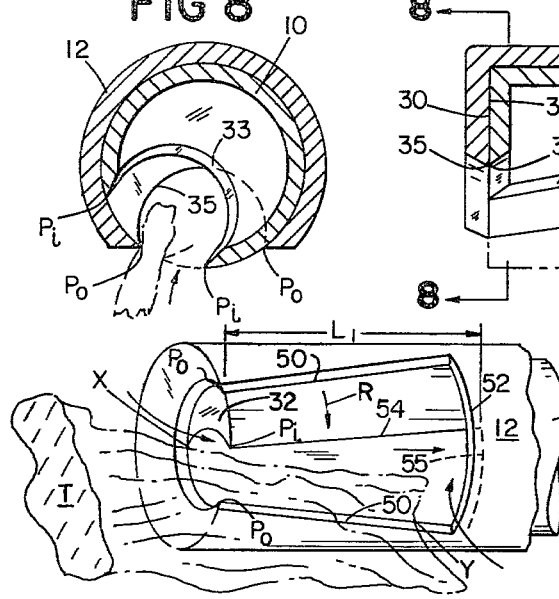
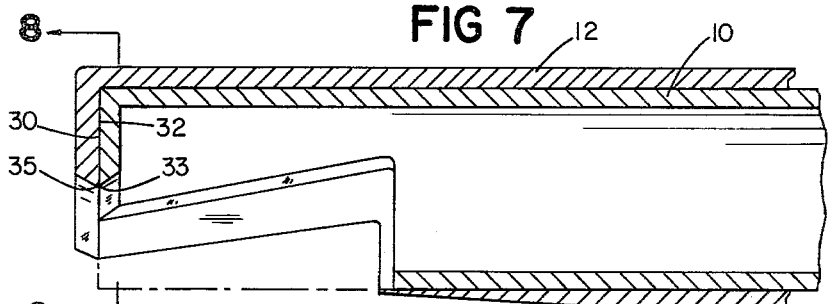
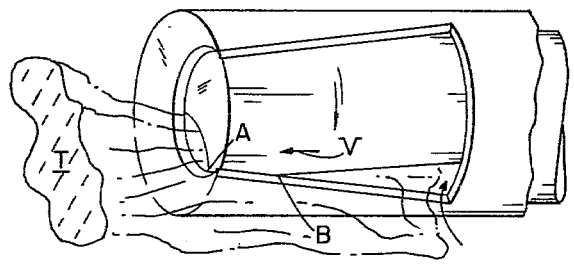
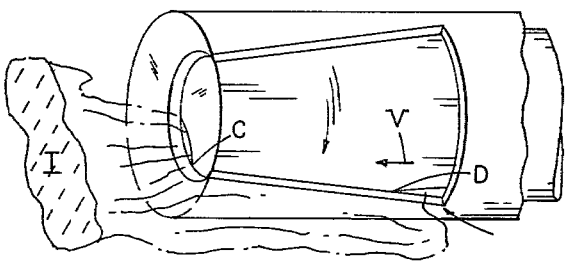
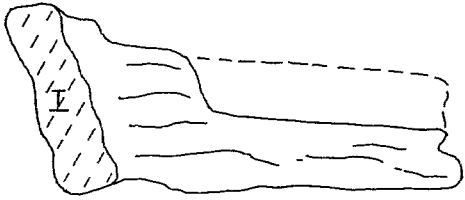
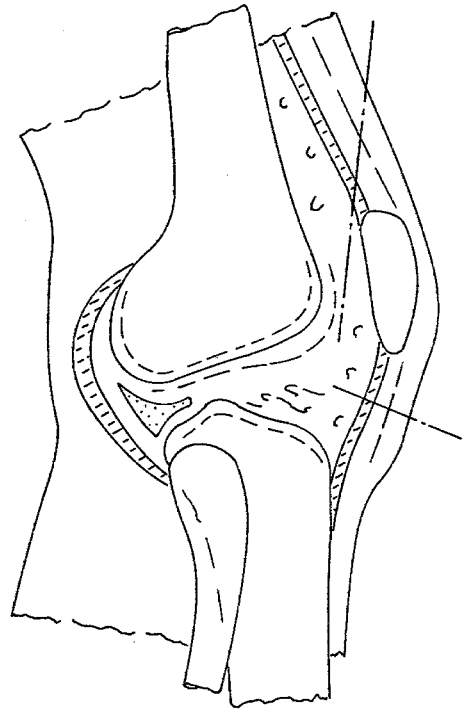

SURGICAL INSTRUMENT

INTRODUCTION

This invention concerns an improved surgical instrument of the remote cutting type, in which an inner tubular member having a cutting edge rotates within an outer tubular member with a coacting edge, while vacuum is applied, through the instrument, to the cutting site.

BACKGROUND

Instruments of this type have been proposed for surgery in sites of the body that are difficult to make accessible. However, these instruments appear to have serious deficiencies preventing their use on rubbery and tough substances such as cartilage, hence many important surgical procedures have not been possible. Prior efforts in the field are represented, in the patent literature by U.S. Pat. Nos. 2,369,925; 3,618,611; 3,732,858 and 3,844,272 and in commerce by the interarticular shaver sold by Dyonics, Inc., corresponding to copending U.S. application Ser. No. 848,982 by Bonnell.

SUMMARY OF THE INVENTION

Coaxial inner and outer tubes of the instrument have coacting cutting edges in a distal region, the inner tube being rotatably driven while the outer tube is stationary, and means to maintain fluid flow from this region through the instrument.

The invention features an initial cutting point at which cutting portions of the tubes first come together during a cutting cycle, this point defined at the distal extremity of the side of the tubes, and there being cutting edges that extend from this initial point longitudinally along the sides of the tubes, whereby following initiation of gripping and cutting at a point spaced inwardly on the tissue from the exposed tissue edge, cutting can proceed proximally. In an instrument capable of severing discrete pieces of cartilage, cutting edges also extend transversely across the ends of the tubes and cutting proceeds from the initial point in two angular directions toward the exposed edges of the tissue to complete the cut.

Preferred embodiments feature instruments wherein, viewed from the end of the tubes: the initial point of cutting is defined by oppositely directed, pointed portions of the ends of the tubes; the initial cutting point defined by cusp-shaped portions; and with ends of the tubes having substantially flat end closures set substantially at a right angle to the axes of the tubes, the mating cutting edges in the ends of the tubes are of the form of substantially circular arcs having centers that are eccentric relative to the axes of the tubes. Preferred embodiments also feature instruments wherein, viewed from the side of the tubes: the initial point of cutting is defined by the intersection of elongated edges on the respective tubes, these edges set at a diverging angle to each other in the direction away from the distal end; and each cutting edge along the side of a tube extending in a plane angled to the plane which projects through the axis of the tube and through the respective initial cutting point. Also in preferred embodiments the instrument defines two initial cutting points corresponding to respectively opposite directions of rotation; at the end of the tubes both of the initial points of cutting are defined by cusp-shaped portions, preferably the cutting edges of the ends of the tubes corresponding to circular arcs; and preferably when viewed from the side, each tube defines a pair of elongated cutting edges which diverge from each other longitudinally in the direction away from their respective cutting points; preferably each such pair of cutting edges is joined by a transversely extending proximal edge.

BRIEF DESCRIPTION OF THE DRAWINGS

FIG. 1 is a longitudinal, cross-sectional view of the preferred embodiment;

FIG. 2 is an end view taken on line 2—2 of the preferred embodiment;

FIG. 3 is an exploded view of the instrument of FIG. 1 on a reduced scale along with other instruments used in a surgical procedure;

FIG. 4 is a plan view partially in cross-section of the knee joint of a human with broken lines indicating directions of access for the instrument;

FIG. 4a is a side view of the knee of FIG. 4;

FIG. 5 is a side view of the distal end of the instrument of FIG. 1 on an enlarged scale;

FIG. 6 is an end view of FIG. 5;

FIG. 7 is a longitudinal, cross-sectional view taken on line 7—7 of FIG. 5;

FIG. 8 is a transverse, cross-sectional view taken on line 8—8 of FIG. 7; and

FIGS. 9, 9a, 9b, and 9c are perspective views, partially diagrammatical, illustrating the cutting action of the instrument.

PREFERRED EMBODIMENT

Referring to FIG. 1, inner and outer tubes 10 and 12 extend from their distal cutting region D, at the surgical site, over length L to handle/motor assembly 14. The outer tube 12 is fixed to outer body 16 by intermediate end member 17. The inner tube 10 extends beyond end 17 to attachment 18. This attachment has transverse evacuation passages 20, end abutment surface 22 engated by spring 24, and a drive extension 26 which is engaged with the motor drive shaft 28. Spring 24 urges the inner tube 10 to the left so that distal end surface 32 of the inner tube (FIG. 7) continually bears against the distal end surface 30 of the outer tube. This maintains a proper cutting relationship between end cutting edges 33, 35. Motor 31 in the housing propels drive shaft 28. The body 16 has a suction exit port 19 connected to a conventional suction line. Fluid and cut particles from the surgical site are thus drawn through the inner tube 10, passage 20 and exit port 19. A battery 34 (FIG. 3) is remote from the motor and foot switch. This power pack is activated by foot pedal 36 in the conventional way.

The cutting instrument is used with illuminating-/viewing instrument 40 (FIG. 3) comprised of a probe 42 containing light conductive glass fibers and an image-transmitting endoscope lens system. Through the glass fibers light from a light source 44 is conducted to the surgical site and through lens system an image is conducted back from the site to video camera 46. The camera produces a continual view of the surgical site on video monitor 48 which the surgeon views while he manipulates the instruments to perform the desired surgery.

For surgery of the knee, for instance, the surgical instrument is introduced to the surgical site along the lines of access such as indicated in FIGS. 4 and 4a while the illuminating/viewing instrument 40 is introduced along another line of access so that the end of the instrument can be viewed continually. Saline is introduced along another line to extend the joint cavity. Entry to the surgical site is achieved through tiny incisions made by a trocar 48 acting through a cannula 51. After the incision, with the cannula in place, the trocar is withdrawn and the respective instrument is inserted through the cannula (see FIG. 1). The instrument has the unique ability of removing cartilage such as the miniscal cartilage between bones of the knee, as is suggested by these views. In FIG. 2, two end views of the instrument are shown. At the left the pointed cutting edges are shown coming together in tong-like action on a portion of tissue. At the right, rotation of the inner tube has caused the cut to be completed.

Referring to enlarged scale FIGS. 5 through 9, the outer tube 12 and the inner tube 10 are closed by substantially planar end surfaces 30 and 32. Bearing of end surface 32 against end surface 30 is achieved by action of the spring 24 (FIG. 1) to ensure proper relation of the end cutting edges. Close-fitting of the tubes similarly assures proper relation of the side cutting edges. To define these cutting edges both tubes have end and side openings. The details of openings, initial cutting point and cutting edges will now be described.

Initial Cutting Point and Cutting Edges

Although the embodiment shown is for cutting in both directions of rotation, description will first be given for direction of rotation R of FIGS. 9–9a. Referring to FIG. 9, fixed outer tube 12 defines a fixed distally-extreme cutting point $P_o$, formed by cut away of the side wall of the tube. An elongated cutting edge 50 bordering the opening is defined by the wall of the tube. It extends longitudinally from point $P_o$, in a plane set at a downward angle to a plane projected through point $P_o$ and the axis of the tube. Edge 50 extends distance L, and terminates at transverse edge 52, which also borders the opening and is formed by the wall of the tube.

The end plate of the outer tube, which defines the end bearing surface 30, is cut away to define the end cutting edge 35. The cut is of circular form, commencing at point $P_o$ and of radius substantially less than the radius of the outer tube so that the opening is eccentric to the axis of the tube.

The inner tube 10 has a corresponding shape. From the distally extreme point $P_i$, an elongated cutting edge 54 borders the opening in, and is defined by the wall of the inner tube 10. It lies in an upwardly angled plane relative to a plane projected through point $P_i$ and the axis of the tube. Edge 54 also extends for length $L_1$, and beyond, terminating in a transverse edge 55, formed in the wall of inner tube 10, beyond the transverse edge of the outer tube.

Thus the inner and outer side-cutting edges are set at an angle to each other. When points $P_o$ and $P_i$ coincide, the edges diverge in the proximal direction.

Referring to FIG. 5 it will be seen that the side of the outer tube is constructed symmetrically about a plane through the tube axis. Thus edge 50a extends from upper point $P_o$ at an angle, diverging with respect to edge 50, until it terminates at transverse edge 52, so that the width of the opening in the side of the tube increases in the proximal direction.

The side of the inner tube is identically constructed with an edge (not shown) diverging in the proximal direction from edge 54 until it terminates at the proximal transverse edge 55.

The ends of the inner and outer tubes are each characterized by the arcuate cutting edge extending from on peripheral point to the other, thus defining a crescent-shaped cutting edge terminating at two cusp-shaped points at the periphery.

In a typical instrument useful for removing the miniscal cartilage of the knee the outer diameter of the inner tube 10 and the matching inner diameter of the outer tube 12 is approximately 0.135 inch with slight running clearance, the wall thicknesses is approximately 0.010 inch, and the tubes are made of stainless steel. The outer tube length, L, is approximately 4 inches. The length, $L_1$ of the side cutting edge 50 of the outer tube 12, is approximately ¼ inch, the length of the edge 54 of the inner tube is 5/16 inch, the radius of the end cutting edge 35 is approximately 0.040 inch, and the radius of end cutting edge 33 is approximately 0.035 inch. The space between the opposed points $P_o$ and $P_i$ is approximately 0.025 inch.

Operation

In FIG. 9 the distal end of the instrument has been positioned to cut tissue T. The instrument is shown with the edge of the tissue extending through the instrument from point X to point Y, with the distally extreme fixed point $P_o$ of the outer tube engaging the tissue spaced from the tissue edge. In FIG. 9 the point $P_i$ of the inner tube is shown closing toward point $P_o$ of the outer tube in a motion similar to that of a grasping forceps.

As the motion proceeds these points first firmly grasp the middle of the tissue and then progressively cut it. In FIG. 9b $P_i$ has passed $P_o$ in an initial scissors-like severing of the tissue, this cutting action proceeding to radiate in two directions from this initial point. In FIG. 9a the instantaneous point of scissors-like cutting occurs at end and side points A and B and, in later FIG. 9b, at end and side points C and D. With slightly more rotation the cut is complete, and if the instrument is withdrawn, as depicted in FIG. 9c, the portion indicated is seen to have been cut away.

The location of the initial cutting point in the distal extremity of the side of the tube provides a number of advantages that make cutting of rubber-like cartilage possible. The tongs or forceps-like initial contact captures the tissue and prevents it from being forced away from the instrument. The two-way angled cutting that then proceeds provides a balanced action, which is found simultaneously to avoid problems of stalling, ensures decisive severing, and prevents undue deflections.

From the beginning of the cut the reaction force from the side cut, e.g. at points B and D, acts on the inner tube in the distal direction of vector $v$, tending to urge the inner tube to bear against the end of the outer tube. This effect tends to overcome a reaction force in the opposite direction applied at end points A and C on the inner tube.

Rotation in opposite direction by reversal of the motor direction as by the foot switch, produces the same cutting action, by the opposite points and cutting edges of the instrument.

What is claimed is:

1. In a surgical instrument of the type comprising coaxial inner and outer tubes having coacting cutting edges in a distal region, the inner tube being rotatably driven while the outer tube is stationary, and means to maintain fluid flow from the cutting region through the instrument, the improvement wherein a limited segment of the side of each tube is open, said opening of each tube extending to the distal extremity of the side of said tube, and at least the portion of the end of each tube that corresponds with the respective opening in the side of the tube being open, whereby at a first position of rotation of the inner tube, body tissue can protrude through the end and side openings of said tubes into the volume of the inner tube, said tubes bounding said side openings defining initial tissue-penetrating sharp pointed portions located where the tubes first come together during rotation of said inner tube, said pointed portions located at the distal extremity of the sides of the tubes, and cutting edges extend from said initial tissue-penetrating pointed portions both transversely across the end of and longitudinally along the sides of the tubes, whereby following initiation of gripping and cutting at said pointed portions located inwardly on the tissue from an exposed edge of the tissue, cutting can proceed in two angular directions toward the exposed edge of the tissue to complete the cut.

2. In a surgical instrument of the type comprising coaxial inner and outer tubes having coacting cutting edges in a distal region, the inner tube being rotatably driven while the outer tube is stationary, and means to maintain fluid flow from the cutting region through the instrument, the improvement wherein a limited segment of the side of each tube is open, said opening extending to the distal extremity of the side of said tube, and at least the portion of the end of each tube that corresponds with the respective opening in the side of the tube being open, whereby at a first position of rotation of the inner tube, body tissue can protrude through the end and side openings of said tubes into the volume of the inner tube, said tubes bounding said side opening defining initial tissue-penetrating sharp pointed portions located where the tubes first come together during rotation of said inner tube, said pointed portions located at the distal extremity of the sides of the tubes, and cutting edges extend from said initial tissue-penetrating pointed portions longitudinally along the sides of the tubes, whereby following initiation of gripping and cutting at said pointed portions located inwardly on the tissue from an exposed edge of the tissue, cutting can proceed proximally.

3. The surgical instrument of claim 1 or 2 wherein viewed from the side of the tubes, the initial point of cutting is defined by the intersection of elongated edges on the respective tubes, said edges set at an angle diverging from each other in the direction away from the distal end.

4. The surgical instrument of claim 3 wherein a cutting edge along the side of a tube extends in a plane angled to the plane which projects through the axis of the tube and through the respective initial cutting point.

5. The surgical instrument of claim 1 or 2 wherein the instrument defines two of said initial cutting points corresponding to respectively opposite directions of rotation.

6. The surgical instrument of claim 5 wherein each tube viewed from the side defines a pair of elongated cutting edges which diverge from each other longitudinally in the direction away from their respective cutting points.

7. The surgical instrument of claim 6 wherein a pair of cutting edges in a tube are joined by a transversely extending proximal edge, said cutting edges and said proximal edge bounding an opening in the side of the tube.

8. The instrument of claim 1 or 2 wherein, viewed from the end of the tubes the initial point of cutting is defined by oppositely directed, pointed portions of the ends of the tubes.

9. The instrument of claim 1 wherein said pointed portions are cusp-shaped.

10. The instrument of claim 9 wherein at their ends the tubes have substantially flat end closures set substantially at a right angle to the axes of the tubes, and the mating cutting edges in the ends of said tubes are in the form of substantially circular arcs having centers that are eccentric relative to the axes of the tubes.

11. The surgical instrument of claim 1 wherein the instrument defines two of said initial cutting points corresponding to respectively opposite directions of rotation, and wherein, viewed form the end of the tubes, both of said initial points of cutting are defined by cusp-shpaed portions, the cutting edges of the ends of said tubes corresponding to circular arcs.

12. The surgical instrument of claim 11 wherein each tube, viewed from the side, defines a pair of elongated cutting edges which diverge from each other longitudinally in the direction away from their respective cutting points.

* * * * *